United States Patent [19]

Masters

[11] Patent Number: 4,669,456
[45] Date of Patent: Jun. 2, 1987

[54] POSITIONABLE PENILE PROSTHESIS
[75] Inventor: Gene P. Masters, Bogart, Ga.
[73] Assignee: Mentor Corporation, Minneapolis, Minn.
[21] Appl. No.: 491,518
[22] Filed: May 4, 1983
[51] Int. Cl.[4] ............................................. A61F 5/00
[52] U.S. Cl. ..................................... 128/79; 623/11
[58] Field of Search ................. 128/79, 772; 3/1; 604/95, 170, 281, 282; 273/84 R; 138/153, 174, 144; 623/11

[56] References Cited

U.S. PATENT DOCUMENTS

| | | | |
|---|---|---|---|
| 419,926 | 1/1890 | Chapman | 604/282 |
| 2,211,975 | 8/1940 | Hendrickson | 604/282 |
| 2,268,321 | 12/1941 | Flynn | 604/282 |
| 3,426,744 | 2/1969 | Ball | 604/282 |
| 3,498,286 | 3/1970 | Polanyi | 604/282 |
| 3,526,086 | 9/1970 | Morgan | 138/153 |
| 3,618,613 | 11/1971 | Schulte | 604/282 |
| 3,987,789 | 10/1976 | Timm | 3/1 |
| 4,066,073 | 2/1978 | Finney | 128/79 |
| 4,140,154 | 2/1979 | Kanao | 138/174 |
| 4,151,840 | 5/1979 | Barrington | 128/79 |
| 4,175,992 | 11/1979 | Grawey | 138/144 |
| 4,184,497 | 1/1980 | Kolff et al. | 604/282 |
| 4,187,839 | 2/1980 | Nuwayser | 128/79 |
| 4,411,260 | 10/1983 | Koss | 128/79 |

Primary Examiner—Stephen C. Pellegrino
Attorney, Agent, or Firm—Kinney & Lange

[57] ABSTRACT

An implantable, positionable penile prosthesis which comprises an elastomeric rod and a metal wire coil coaxially imbedded within at least a portion of the rod. The coil has a radius, number of turns per unit length, and wire diameter which combines with the elastomeric rod for substantially retaining the position into which the prosthesis is bent and for inhibiting fatigue of the metal wire coil when the prosthesis is repeatedly bent for positioning.

35 Claims, 15 Drawing Figures

FIG. 10

FATIGUE-LIFE CURVE FOR STERLING Ag

POSITIONABLE PENILE PROSTHESIS

BACKGROUND OF THE INVENTION

This invention is directed to an implantable, positionable penile prosthesis which has use for the treatment of erectile impotence.

Impotence is not only physiologically based, but can be related to nerve or vascular damage that may have been caused by severe diabetes, multiple sclerosis, spinal cord injury or surgery in the lower abdomen, such as removal of the bladder or for rectal cancer, or it can also be the result of advanced age, trauma and the side effects of medicines and drugs.

Today there are currently two types of penile prostheses that are commercially available. The two types of prostheses are the simple implantable prosthesis generally implanted in pairs in the corpora cavernosa of the penis and the inflatable, implantable penile prosthesis also implanted within the corpora cavernosa, but connected to a hydraulic pumping device implanted elsewhere in the patient's body, such as the scrotum.

The noninflatable prosthesis is generally implanted within the corpora cavernosum of the penis. This area of the penis is the cavity which receives a volume of blood for causing an erection. When the noninflatable prostheses are implanted within the corpora cavernosum, there is provided a generally constant erection as the prosthesis substantially fills the corpora cavernosum. The inflatable prosthesis has an advantage over the noninflatable prosthesis as the inflatable prosthesis can be either inflated or deflected to provide an erect penis or flacid penis. Thus, the inflatable prosthesis more nearly approximates the natural conditions. It is desirable in the noninflatable prosthesis to provide positionability to the prosthesis. That is, it is desirable to provide positionability so that the constant erection of the penis can be easily concealed by the patient. Methods and prostheses to provide positionability have been developed and include inserting metal rods in the prosthesis or providing various hinging mechanisms within the prosthesis. A problem encountered with such prostheses is that they are not easily positioned, and those that are, can tend to fatigue to the extent that rupture of the hinging mechanism or metal rod can occur. Upon rupture, the hinging mechanism or metal rod insert can penetrate the softer sidewall of the prosthesis, thereby necessitating its removal prior to causing serious damage to the tissue.

SUMMARY OF THE INVENTION

The positionable, implantable penile prosthesis herein is a noninflatable penile prosthesis. The prosthesis is designed to be implanted in pairs within the corpora cavernosa of the penis. The prosthesis herein comprises an elastic rod having a metal coil imbedded within a portion of the elastic rod. The invention herein is also directed to a method of constructing a positionable, implantable penile prosthesis comprising an elastic rod having a metal coil imbedded within a portion thereof.

DETAILED DESCRIPTION

The description of the positionable, implantable penile prosthesis which is the subject matter of the invention herein will be described with regard to the accompanying figures.

Figures 1, 2, 3, 4:
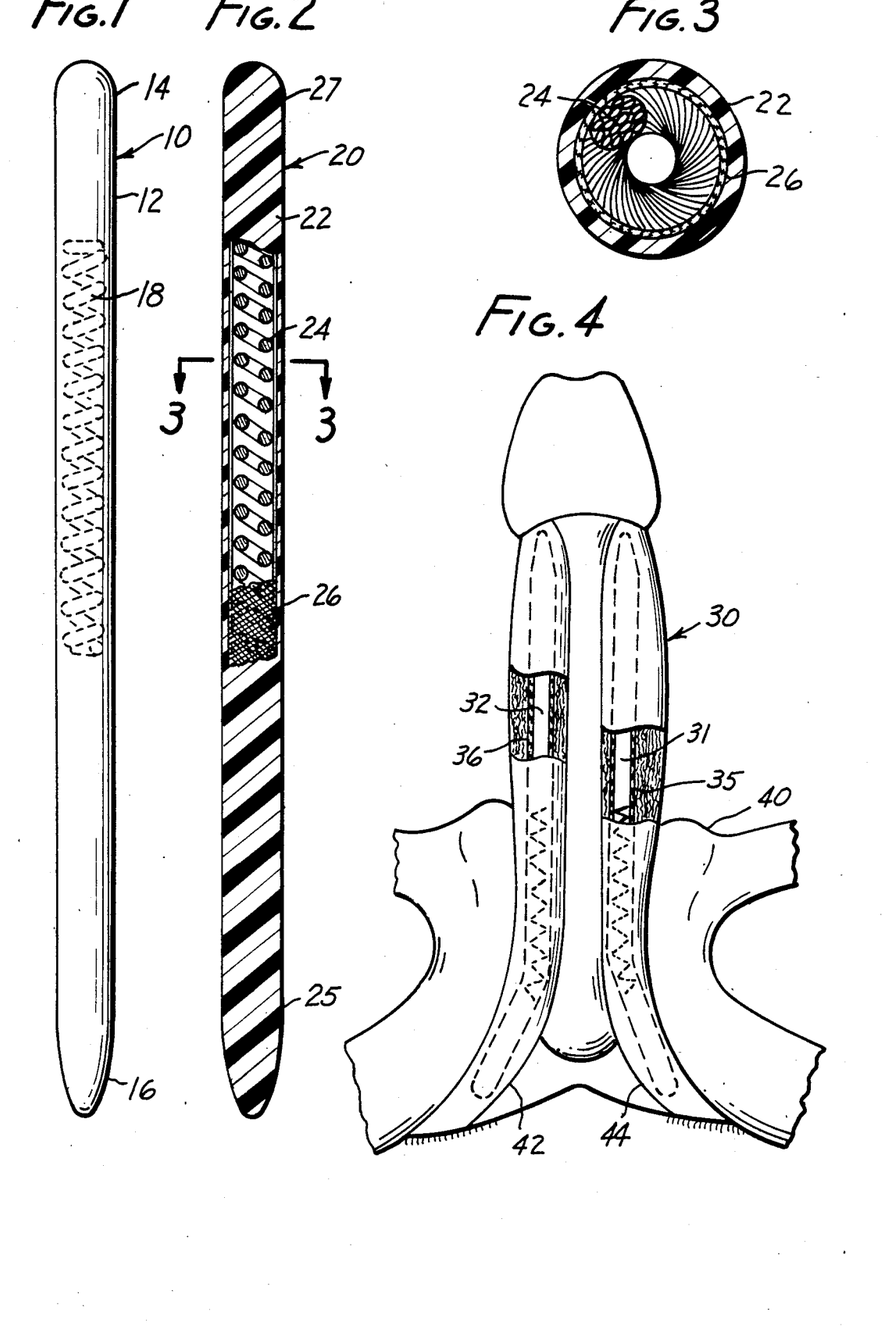
FIG. 1 is an elevational view of one embodiment of the positionable, implantable penile prosthesis herein.
FIG. 2 is an elevational view partially in section of another embodiment of a positionable, implantable penile prosthesis herein.
FIG. 3 is a cross-sectional view of the embodiment shown in FIG. 2 taken along lines 3—3 in FIG. 2.
FIG. 4 is a partially perspective and cutaway view illustrating the positionable penile prosthesis herein implanted within the penis.

With reference to FIG. 1, one embodiment of a positionable prosthesis 10 is disclosed. The positionable prosthesis 10 comprises an elastomeric rod 12 having a distal end 14 and a proximal end 16. Imbedded within the elastomeric rod is a metal spring 18.

At the time of the invention herein, there was available an implantable penile prosthesis which comprised an elastomeric rod having a braided wire rod imbedded therein. Basically, such a structure is disclosed in U.S. Pat. No. 3,987,789 of Gerald W. Timm which discloses a braided wire rod penile prosthesis. A problem with such a prosthesis is that upon continued bending of the prosthesis and braided wire imbedded therein, the braided wire fatigues and ruptures. Upon rupture of the braided wire, the wire is able to penetrate the elastomeric body portion of the prosthesis. As the prosthesis is implanted within the penis, it is highly undesirable to have the inner metal wire protruding through the softer outer elastomeric body of the prosthesis as it can cause injury to the tissue of the penis and necessitate surgery to remove the implant.

The implantable penile prosthesis having a metal stranded wire or rod inserted therein does provide positionability and this positionability is a desirable feature in implantable penile prosthesis. However, the strain on the metal or braided wire rod within the prosthesis because of repeated positioning can cause fatigue and is undesirable. It would be desirable to construct a positionable penile prosthesis which would be positionable through various forces applied thereto, but which would not fatigue under such forces. The positionable, implantable penile prosthesis herein is capable of providing positionability under sufficient force to position the penis, but which resists fatigue to a greater extent than the braided wire or metal rod type of prosthesis.

The positionable prosthesis herein comprises an elastic body 12 having a proximal end 14 and a distal end 16.

As used herein, the term proximal will mean the end that is positioned closest to the heart and the term distal will mean the end that when implanted will be furthest from the heart. Within the elastomeric body portion of the prosthesis is a metal coil or spring 18.

The elastomeric body of the prosthesis can be constructed of any suitable elastomeric material which is biocompatible with the body. For example, elastomeric silicone is a preferred material for the elastomeric body of the prosthesis. Silicone has been proven to be acceptable as a material from which prostheses implanted in the body can be constructed.

Silicone implantable penile prostheses have been known as can be seen by the teachings of Small et al in U.S. Pat. No. 3,893,456.

The metal coil or spring 18 provides the positionability to the penile prosthesis. However, not all springs provide such positionability. In addition, not all springs will provide the necessary fatigue life so as to have utility in an implantable penile prosthesis. Thus, there are certain physical characteristics and criteria for the metal coil or spring which is to be used within the elastomeric body of an implantable penile prosthesis to provide positionability and utility.

A metal coil has been selected as being an improvement over a metal rod after having determined that the fatigue life for a coil is greater than that of a rod as will be shown by the following calculations.

Figures 5, 6, 7, 8, 9:
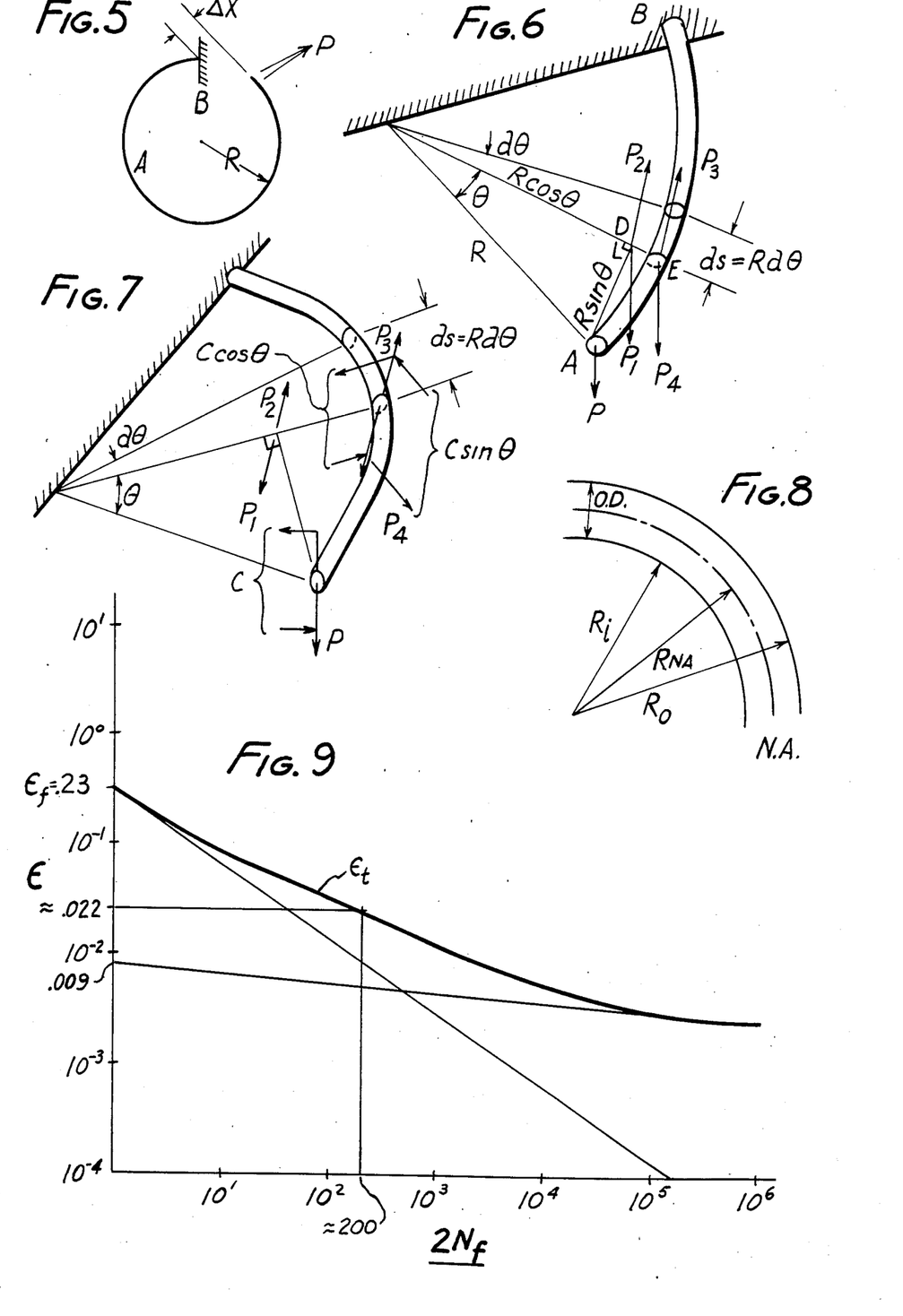
FIGS. 5-8 are diagrammatical views of a single loop of a metal coil illustrating the relationship between certain variables considered in the present invention.
FIG. 9 is a graphical illustration of empirically determined data for use in determining fatigue life.

With reference to FIGS. 5 and 6, for a single loop the following forces and stresses have been found. With reference to FIG. 6 wherein P equals the applied force, U the total energy, the moment at any point E will be given then by the formula:

$$M = PR \sin \theta$$

and the direct shear $$U = P$$

and the torsion is given by the formula $$T = PR(1 - \cos \theta)$$

The deflection then is $$\delta_A = \delta U / \delta P$$

and the potential energy and kinetic energy is given by the formula:

$$U_{ds} \tfrac{1}{2}(M^2/EI)ds + \tfrac{1}{2}(T^2/JG)ds + \tfrac{1}{2}(U^2/Ga)ds$$

then $$U_T = \int_0^l \tfrac{1}{2} \frac{M^2}{EI} ds + \int_0^l \tfrac{1}{2} \frac{T^2}{JG} ds + \int_0^l \tfrac{1}{2} \frac{U^2}{Ga} ds$$

The deflection at A:

$$\delta_A = \frac{\delta U}{\delta P} = \int_0^l \frac{M}{EI} \frac{\delta}{\delta} \frac{M}{P} ds +$$

$$\int_0^l \frac{T}{JG} \frac{\delta}{\delta} \frac{T}{P} ds + \int_0^l \frac{U}{Ga} \frac{\delta U}{\delta P} ds$$

but $$\delta M / \delta P = R \sin \theta; \quad M/EI = (PR \sin \theta)/(EI); \quad ds = R d\theta$$

and $$\delta T / \delta P = R(1 - \cos \theta);$$

$$\frac{T}{JG} = \frac{PR(1 - \cos \theta)}{JG}$$

and $$\delta U / \delta P = 1$$

and $$U/Ga = P/Ga$$

thus substituting $$\delta_A = \int_0^{\pi/2} \frac{PR^3}{EI} \sin^2 \theta \, d\theta +$$

$$\int_0^{\pi/2} \frac{PR^3}{JG} (1 - \cos \theta)^2 \, d\theta + \int_0^{\pi/2} \frac{PR}{aG} \, d\theta$$

which equals $$(PR^3/EI)[\{\tfrac{1}{2}\theta - \tfrac{1}{4} \sin 2\theta\}_0^{\pi/2}] + (PR^3/JG)[\theta - 2 \sin \theta + \tfrac{1}{2}\theta + \tfrac{1}{4} \sin 2\theta\}_0^{\pi/2}] + (PR\pi/2Ga)$$

which equals $$\frac{PR^3}{EI} \left( \frac{\pi}{4} - 0 \right) + \frac{PR^3}{JG} \left( \frac{3\pi - 8}{4} \right) + \frac{PR\pi}{2Ga}$$

Then for a full loop, the same basic integral applies: If $\Delta X$ equals the increased distance between points on the coil, then $$\delta_A = \Delta X = \int_0^{2\pi} \frac{PR^3}{EI} \sin^2 \theta \, d\theta +$$

$$\int_0^{2\pi} \frac{PR^3}{JG} (1 - \cos \theta)^2 \, d\theta + \int_0^{2\pi} \frac{PR}{aG} \, d\theta$$

which equals $$PR^3/EI[\{\tfrac{1}{2}\theta - \tfrac{1}{4} \sin 2\theta\}_0^{2\pi}] + PR^3/JG[\{\theta - 2 \sin \theta + \tfrac{1}{2}\theta + \tfrac{1}{4} \sin 2\theta\}_0^{2\pi}] + (PR/Ga)2\pi$$

which is equal to $$(PR^3/EI)[\pi - 0] + (PR^3/JG)[2\pi - 0 + \pi + 0] + (PR/Ga)2\pi$$

knowing and substituting the following $$I = \pi r^4/4$$

$$J = 2\pi r^4/4$$

and $$a = \pi r^2$$

then substituting $$\delta_A = \frac{4PR^3\pi}{\pi r^4 E} + \frac{12\pi PR^3}{2\pi r^4 G} + \frac{2\pi PR}{G\pi r^2}$$

$$= \frac{PR^3}{r^4}\left(\frac{4}{E} + \frac{6}{G}\right) + \frac{2PR}{Gr^2} =$$

$$\frac{2PR}{r^2}\left(\frac{2R^2}{r^2 E} + \frac{3R^2}{r^2 G} + \frac{1}{G}\right)$$

which equals $$\frac{2PR}{r^2}\left(\frac{2R^2}{r^2 E} + \frac{3R^2 + r^2}{r^2 G}\right)$$

which equals $$\frac{2PR}{r^4}\left(\frac{2R^2}{E} + \frac{3R^2 + r^2}{G}\right)$$

which is the total increased separation of two matching points on a coil loop due to applied force P.

Now the angle of twist at the end of the coil is calculated as follows and with regard to FIG. 7. An artificial couple C is introduced at the end of the length of the coil. Thus we have $$M = PR\sin\theta - C\sin\theta = [PR - C]\sin\theta$$

and $$T = PR[1 - \cos\theta] + C\cos\theta$$

and $$U = P$$

$$U = \int_0^l \tfrac{1}{2}\frac{M^2}{EI}ds + \int_0^l \tfrac{1}{2}\frac{T^2}{JG}ds + \int_0^l \tfrac{1}{2}\frac{U^2}{Ga}ds$$

$$U = \frac{R}{2EI}\int_0^{\pi/2}(PR - C)^2\sin^2\theta\,d\theta +$$

$$\frac{R}{2JG}\int_0^{\pi/2}\{PR(1 - \cos\theta) + C\cos\theta\}^2 d\theta + \frac{P^2R}{2Ga}\int_0^{\pi/2}d\theta$$

The angle of twist is equal to $\Omega$
and $$\Omega_A = \delta U/\delta C$$

solving for $$\Omega_A = \frac{\delta U}{\delta C} = -\frac{R}{EI}\int_0^{\pi/2}(PR - C)\sin^2\theta(d\theta) +$$

$$\frac{R}{JG}\int_0^{\pi/2}\{PR(1 - \cos\theta) + C\cos\theta\}\cos\theta\,d\theta + \frac{\delta U}{\delta C}$$

but $\delta U/\delta C$ approaches zero
which is equal to $$-\frac{R}{EI}\left\{(PR - C)\left(\frac{\theta}{2} - \frac{1}{4}\sin 2\theta\right)\right\}_0^{\pi/2} +$$

$$\frac{R}{JG}\left\{PR\sin\theta + (C + PR)\left(\frac{\theta}{2} + \frac{1}{4}\sin 2\theta\right)\right\}_0^{\pi/2}$$

is equal to $$-\frac{\pi}{4}\frac{PR^2 - RC}{EI} + \frac{R}{JG}\left\{PR + (C - PR)\frac{\pi}{4}\right\}$$

but
C=0 since it is fictitious
and $$J = 2I = 2\pi r^4/4$$

therefore $$\Omega_A = -\frac{\pi}{4}\frac{PR^2}{EI} + \frac{R}{JG}\left\{PR - PR\frac{\pi}{4}\right\} =$$

$$-\frac{\pi}{4}\frac{PR^2}{EI} + \frac{PR^2}{JG}\left(\frac{4 - \pi}{4}\right)$$

which is equal to $$\frac{2PR^2}{\pi r^4 G}\left(\frac{4 - \pi}{4}\right) - \frac{\pi}{4}\frac{4PR^2}{E\pi r^4} = \frac{PR^2}{r^4}\left(\frac{4 - \pi}{2\pi G} - \frac{1}{E}\right)$$

which is equal to $$\frac{PR^2}{r^4}\left\{\left(\frac{2}{\pi} - \frac{1}{2}\right)\frac{1}{G} - \frac{1}{E}\right\}$$

The angle of twist then for a half loop ($\pi$ radians):

$$\Omega = -\frac{R}{EI}\left\{(PR - C)\left(\frac{\theta}{2} - \frac{1}{4}\sin 2\theta\right)\right\}_0^{\pi} +$$

$$\frac{R}{JG}\left\{PR\sin\theta + (C + PR)\left(\frac{\theta}{2} + \frac{1}{4}\sin 2\theta\right)\right\}_0^{\pi}$$

is equal to $$-\frac{R}{EI}\left\{(PR - C)\left(\frac{\pi}{2}\right)\right\} +$$

$$\frac{R}{JG}\left\{0 + (C + PR)\left(\frac{\pi}{2} + 0\right)\right\}$$

is equal to $$-\frac{PR^2 - RC}{EI}\frac{\pi}{2} + \frac{PR^2 + CR}{JG}\frac{\pi}{2}$$

but remember

C=0
therefore $$\Omega = \frac{PR^2}{JG}\frac{\pi}{2} - \frac{PR^2}{EI}\frac{\pi}{2}$$

which is equal to $$\frac{4PR^2}{2\pi r^4 G}\frac{\pi}{2} - \frac{4PR^2}{\pi r^4 E}\frac{\pi}{2}$$

which is equal to $$\frac{PR^2}{r^4}\left(\frac{1}{G} - \frac{2}{E}\right)$$

The angle of twist for a full loop ($2\pi$):

$$\Omega = -(R/EI)\{[PR-C]\pi\} + (R/JG)\{0 + [C+PR][\pi + 0]\}$$

is equal to $$-\frac{PR^2 - RC}{EI}\pi + \frac{CR + PR^2}{JG}\pi$$

is equal to $$\frac{2PR^2}{r^4}\left(\frac{1}{G} - \frac{2}{E}\right)$$

With reference to FIG. 8, $\Delta X$ is calculated as follows. The length of the neutral axis in the section having a 90° bend is represented by $l_{NA}$ thus $l_{NA}$ = circumference/4 = C/4

$C = 2\pi R_{NA}$ or $R_{NA} = C/2\pi$ and
$R_0$
is equal to the outside radius is equal to $R_{NA} + (O.D.)/2$ The elongation of the outer fibers is then given by $$\Delta X_t = \frac{2\pi R_0}{4} - l_{NA}$$

$\Delta X$ per each loop is equal to $\Delta X_t / N$ then $$\Delta X_t = 2\pi\left(\frac{4l_{NA}}{2\pi} + \frac{O.D.}{2}\right) - l_{NA}$$

which is equal to $$\frac{4l_{NA} + \pi\, O.D.}{4} - l_{NA}$$

which is equal to $\pi/4\ O.D.$ which is equal to $\pi R/2$ or $\Delta X = \pi R/2N$ for a 90° bend, which shall be used as a standard. Remember from above $\Delta X$ for a length of coil N was equal to $$\frac{N2PR}{r^4}\left(\frac{2R^2}{r^2 E} + \frac{3R^2 + r^2}{r^2 G}\right)$$

Therefore, the force $$P = \frac{\frac{r^2 \Delta X}{2RN}}{\frac{2R^2}{r^2 E} + \frac{3R^2 + r^2}{r^2 G}}$$

The bending stress then equals: (from above)

$$\sigma_B = \frac{P(R\sin\theta)\, r^4}{\pi r^4}$$

and the torsion stress is $$\tau_T = \frac{PR(1-\cos\theta)\,4r}{2\pi r^4}$$

and the shear stress is $Y_U = P/\pi r^2$ then simplifying each of the above terms by substituting for P, we have:

$$\sigma_B = \frac{r^2 \Delta X}{2RN}\left(\frac{r^2 E}{2R^2} + \frac{r^2 G}{3R^2 + r^2}\right)\left(\frac{4rR\sin\theta}{\pi r^4}\right)$$

$$= \frac{2\Delta X r\sin\theta}{N\pi}\left(\frac{E}{2R^2} + \frac{G}{3R^2 + r^2}\right)$$

then $$T_T = \frac{r^2 \Delta X}{2RN} \left( \frac{r^2 E}{2R^2} + \frac{r^2 G}{3R^2 + r^2} \right) \left( \frac{4rR(1 - \cos\theta)}{2\pi r^4} \right)$$

$$= \frac{\Delta X r (1 - \cos\theta)}{N\pi} \left( \frac{E}{2R^2} + \frac{G}{3R^2 + r^2} \right)$$

and $$T_U = \frac{r^2 \Delta X}{2RN} \left( \frac{r^2 E}{2R^2} + \frac{r^2 G}{3R^2 + r^2} \right) \frac{1}{\pi r^2}$$

$$= \frac{r^2 \Delta X}{2\pi RN} \left( \frac{E}{2R^2} + \frac{G}{3R^2 + r^2} \right)$$

The maximum $\sigma$ is at 90° from the top of the coil and the maximum Y is at 180°. Both the shear and torsional forces match and separate on a cross-sectional surface, becoming orthogonal and collinear with the bending force. The maximum strain on the coil is at 90° to the plane through which the coil is bent.

To derive the point of maximum stress, various fatigue tests were empirically conducted to determine the location of greatest strain. Through such tests, it was determined that the maximum strain was at 90° to the plane through which the coil is bent.

It is important to note that the stress and strain resistance of a coil can be optimized whereas the stress and strain resistance of a rod cannot. After deriving the above formulas, it can be seen that the stress on a coil is a function of different variables. For example the stress and strain are a function of the following:

(a) The number of coils in the coil by the relationship $f(1/N)$;
(b) Young's modulus and the shear modulus for a specific material by the relationship $f(E)$ and $f(G)$;
(c) To the opening between coils due to bending given by the relationship $f(\Delta X)$;
(d) As a function of the radius of the coil by the relationship $f(1/R^2)$;
(e) As a function of the radius of the rod by the relationship $f(r)$; and
(f) The distance between coils due to opening through bending is itself a function of the radius of the coil which is given by the relationship $\Delta X \alpha f(R)$.

The stress and strain functions given above can be seen to be variable for a coil. As can be seen from the above functions, the stress and strain on a rod is a function of only the functions listed above in subparagraphs b and e. The relationships and ability to optimize the stress and strain provided by the relationships given in the functions in subparagraphs a, c, d, and e provide the ability to optimize stress and strain on a coil without fatigue over a rod.

Both Young's modulus and the shear modulus are material properties and are determined by the selection of the material of which either the rod or coil is constructed. Preferably, a low fatiguing material is chosen in order to optimize the stress and strain. It is desirable that the radius of the coil be as close to the outer surface of the prosthesis as possible. Therefore, it is desirable to select an R being as large as possible, but not so large as to cause an erosion of the coil through the silicone prosthesis. Similarly, it is desirable to select a large number of coils. As can be seen above, the greater the number of coils the lower the stress and strain. However, the number of coils is directly related to the phenomenon of springback and thus the number of coils should be as few as possible. With regard to the radius of the rod forming the coil, it is desirable to select that radius as small as possible, but which will still provide an acceptable stiffness to the coil overall.

To again access the derivations made with regard to a coil and single strand wire, additional fatigue tests were conducted using a solder wire. A solder wire was selected as it was readily ruptured after a relatively few fatigue cycles. The solder wire selected was a 1/16th inch outside diameter 60-40 solder.

In a first tensile test conducted on a single strand solder wire having a length of six inches and an extrapolated elongation of 0.41 inches, the following values were determined:

$\epsilon = \Delta L/L = 0.068$ $\sigma = P/A = 35,595$ psi $E = \sigma/\epsilon = 4.8 \times 10^5$ and $\sigma_{MAX} = 14.2/A = 4,628$ psi In a second experiment, four strands of the 1/16th inch solder wire were twisted together. For this test $\Delta L = 0.074$ $\epsilon = \Delta L/L = 0.0123$ $\sigma = P/A = 100/0.0123 = 8,149$ psi $E = \sigma/\epsilon = 6.6 \times 10^5$ and $\sigma_{MAX} = 31.8/A = 2,591$ psi.

The four stranded silver solder coil had a higher effective E than the single stranded coil, but a much lower $\sigma_{MAX}$.

Additional fatigue tests were conducted on a single strand of 50-50 solder coil having ten loops to the inch. The coil had an outside diameter equal to 0.5 inches with r = 0.3125 inches and $l_{NA} = 1.75$ inches $\Delta X = \pi R/2 = 0.3927$ Then by the formula $$\sigma_B = \frac{2 \Delta X r}{N\pi} \left( \frac{E}{2R^2} + \frac{G}{3R^2 + r^2} \right)$$

wherein $$G = \frac{E}{2(1 + v)} = 1.75 \times 10^5$$

as $\nu = 0.375$
and
$E = 4.8 \times 10^5$
then solving for $\sigma_B$ we find
$\sigma_B = 2,128.8$ psi
then $$\sigma_{MAX} = \frac{\sigma}{2} + \sqrt{2(\sigma_B)^2} = 2,569 \text{ psi (from Mohr's circle)}$$

This corresponds to a force of $F = \sigma A = 7.9$ pounds.

This force is well within the elastic region of the coil.

On a second fatigue test using four strands of the 50-50 solder wire having 3.5 coils to the inch and
$\Delta X = 0.3927$
and
$2R = 0.5$ inches
nominal $r = 0.0442$
then using E and G from a single strand and solving for $\sigma_B$ we find:
$\sigma_B = 8,574$ psi
then solving for $\sigma_{MAX}$ we find:
$\sigma_{MAX} = 10,375$ psi.

During the fatigue tests, it was found that the first strand broke at 234 double cycles, the second strand broke at 299 double cycles and the third and fourth strands broke at 400 double cycles. The strain for the coil is determined by $\sigma/E = 2.2 \times 10^{-2}$ This strain corresponds to about 200 cycles-life which seems to substantially agree with the test data.

In a two wire twisted solder coil fatigue test using a coil of six inches
$\Delta X = 0.393$
$l_{NA} = 1.75$
$r = 0.05$
$r_N = 0.037$
$N = 10.5$
$E = 4.1 \times 10^5$
and
$G = 1.5 \times 10^5$
then solving for $\sigma_B$ we find
$\sigma_B = 4,883$
$\sigma_{MAX} = 5,909$ $\epsilon = \sigma_{MAX}/E = 0.014$ Solving the above using $r_N$ rather than r, we find the values to be
$\sigma_B = 3,585$
$\sigma_{MAX} = 4,338$
$\epsilon = 0.010$ Using the empirically determined graph shown in FIG. 9, it is found that the fatigue life is about 2,000 cycles. Empirically it was determined that failure occurred between 2,480 and 2,600 cycles. These values were evidence of the validity of the extrapolated graphical approach in determining the fatigue life.

After determining that the above derivations and extrapolation technique for determining fatigue life was viable, efforts were directed to developing a prototype of a penile implant using a metal coil which would have sufficient fatigue life to be viable as a penile implant. A sterling silver wire was selected. For the sterling silver wire $A = (0.025/2)^2 \sigma = 4.9 \times 10^{-4}$ The effective length of the wire was six inches, the
O.D. initial $=$ O.D.$_i = 0.025$ inches
and the
O.D. final $=$ O.D.$_f = 0.023$ inches The following table provides the data that was generated from a tensile test conducted on the wire for three separate tests.

| | $\sigma$ | $\Delta L$ | $\epsilon$ | E | $\nu$ | G | $\sigma_f$ | $\epsilon_f$ |
|---|---|---|---|---|---|---|---|---|
| 1 | 203718 | 0.335 | 0.056 | $3.65 \times 10^6$ | 0.3 | $1.36 \times 10^6$ | 42780 | 0.205 |
| 2 | 203718 | 0.3 | 0.05 | $4.07 \times 10^6$ | 0.3 | $1.36 \times 10^6$ | 42780 | 0.203 |
| 3 | 203718 | 0.42 | 0.07 | $2.9 \times 10^6$ | 0.3 | $1.36 \times 10^6$ | 42780 | 0.213 |
| A | | 0.35 | 0.059 | $3.54 \times 10^6$ | | $10^6$ | | 0.207 |

Using the above data to generate a curve and extrapolate for fatigue, it is determined that:

$\epsilon_t = 0.207(2N_f)^{-0.6} + 0.012(2N_f)^{-0.1}$

The value 0.207 and 0.012 were generated from the tensile data in the chart above. The first value represents the plastic strain while the second value in the above formula for $\epsilon_t$ equals the elastic strain. The value $0.012 = \sigma_f/E$ It is noticed that r for a multi-stranded wire coil seems to be equivalent to r of any single strand if the twisted bundle has a radius greater than r. A silver wire coil fatigue test was conducted using a nine stranded coil of twisted 0.025 O.D. wire into a single rope having 1.67 coils to the inch. For this coil, the following values were found:
$r = 0.0125$
$E = 3.54 \times 10^6$
$G = 1.36 \times 10^6$
$R = 0.25$
$l_{NA} = 1.75$
$N = 2.9$ $\Delta X = \sigma R/2 = 0.393$ Using the above values to solve for $\sigma_B$ it is found that
$\sigma_B = 38,335$ psi
However, on a twisted strand the actual stresses are found to be one-half of these values due to the looping over, under and around the neutral axis. Therefore,
$\sigma_B = 19,167$ psi
Then
$\sigma_M$ (from Mohr's circle) $= 23,192$ psi
and $\epsilon = \sigma_M/E = 0.0065$ The failure at 6,891 cycles is plotted on the extrapolated fatigue life graph shown in FIG. 10.

In the fatigue testing for the sterling silver wire, it was found that for a straight wire the first strand broke at 387 cycles and the last strand broke at 534 cycles for a predicted life of 80. When the wire was coiled providing a
$R = 0.148$
and
$N = 4.95$ then
$\epsilon = 1.29 \times 10^{-2}$ The first strand broke at 2,640 and the last strand broke at 2,784 cycles for a predicted life of 400. When the same braided wire had a R=0.1684
and
N=3.325
and
$\epsilon = 1.68 \times 10^{-2}$ then the first strand broke at 1,685 cycles and the last strand broke at 1,946 cycles for a predicted life of 180.

In order for a penile prosthesis to have efficacy, it is desirable that the prosthesis be positionable without springing back to the position from which it is moved. A test has been developed to ascertain the value of various prosthesis. This test is referred to as the "springback test." In the springback test, the prosthesis is bent 90° and if the prosthesis remains at the 90° angle, then it is considered to have 100% springback. The springback of the prosthesis must be balanced with the fatigue life and stress of the coil within the prosthesis to provide a useful prosthesis.

Comparative testing of springback was conducted using a "Jonas-type" prosthesis (braided silver wire), a "Finney-type" prosthesis (no metal core) and a prototype of a prosthesis claimed herein.

For three Jonas-type prostheses which were bent through the following angles, there was an average percentage return given as follows:

30°   16.7%
60°   30.6%
90°   30.3%
120°  34.1%

For three Finney-type prostheses, the average percentage return for the following angles is given as follows:

30°   3.3%
60°   2.2%
90°   3.3%
120°  2.2%

To determine the springback of a penile prosthesis having a coil wire through a silicone outer covering, three prototypes were prepared for such springback testing, along with a prototype having a straight wire. In the prototypes, a 9.8 pph cross-linker and D.C. MDX-4210 silicone was used to form the outer body of the prosthesis. A ten strand sterling silver wire having a radius of 0.025 inches was used as the coil or straight wire. When the stranded wire was coiled, the inner diameter of the coil was 0.155 inches, 0.186 inches and 0.218 inches. The springback results for the tests for the four prostheses are given by the following tables:

| Test | $\theta_B$ | Straight | 0.155 | 0.186 | 0.218 |
|---|---|---|---|---|---|
| 1 | 0 | 0° | 0° | 0° | 0° |
|   | 30 | 2° | 1° | 0° | 1° |
|   | 60 | 8° | 5° | 6° | 6° |
|   | 90 | 30° | 12° | 17° | 19° |
|   | 120 | 45° | 18° | 21° | 28° |
| 2 | 30 | 4° | 1° | 0° | 0° |
|   | 60 | 15° | 7° | 7° | 9° |
|   | 90 | 35° | 14° | 15° | 20° |
|   | 120 | 46° | 19° | 28° | 34° |
| 3 | 30 | 4° | 3° | 1° | 4° |
|   | 60 | 15° | 7° | 5° | 11° |
|   | 90 | 34° | 14° | 14° | 21° |
|   | 120 | 47° | 18° | 23° | 30° |

-continued

| $\theta_B$ | Straight Avg. | 0.155 Avg. | 0.186 Avg. | 0.218 Avg. |
|---|---|---|---|---|
| 30 | 3.3 | 1.7 | 0.3 | 1.7 |
| 60 | 12.7 | 6.3 | 6.0 | 8.7 |
| 90 | 33.0 | 13.3 | 15.3 | 20.0 |
| 120 | 46.0 | 18.3 | 24.0 | 30.7 |

| $\theta_B$ | Straight Avg. % | 0.155 Avg. % | 0.186 Avg. % | 0.218 Avg. % |
|---|---|---|---|---|
| 30 | 11.1 | 5.6 | 1.0 | 5.6 |
| 60 | 21.2 | 11.7 | 11.7 | 14.5 |
| 90 | 36.7 | 15.6 | 17.0 | 22.2 |
| 120 | 38.3 | 15.8 | 20.0 | 25.6 |

After having determined the springback character for the prosthesis, the strain for the three coiled prostheses is determined using the formula $$\sigma_B = \frac{2\Delta Xr}{N\pi}\left(\frac{E}{2R^2} + \frac{G}{3R^2 + r^2}\right)$$

To solve for $\sigma_B$
r=0.0125
$E = 3.54 \times 10^6$
$G = 1.36 \times 10^6$ $\Delta X = \sigma R/2$ Substituting these values, it is found that $$\sigma_B = \frac{2.2 \times 10^4}{NR} + \frac{1.7 \times 10^4}{3NR}$$

and $$\epsilon_{MAX} = \frac{\sigma_B(1.21)}{E} = \frac{9.43 \times 10^{-3}}{NR}$$

For the three coiled prostheses then the following is found:

|   | 0.155 | 0.186 | 0.218 |
|---|---|---|---|
| R | 0.148 | 0.1684 | 0.1892 |
| Coils/In. | 2.83 | 1.9 | 1.47 |
| N | 4.95 | 3.325 | 2.57 |
| RN | 0.7326 | 0.56 | 0.486 |
| E | $1.29 \times 10^{-2}$ | $1.68 \times 10^{-2}$ | $1.94 \times 10^{-2}$ |

After having determined the strain for the three prostheses, a plot of the strain versus the maximum springback can be plotted.

Four additional prostheses were prepared using a 25 durometer silicone body and the 10 strand silver wire having a radius of 0.0125 inches. The following values were determined:

|   | 1 | 2 | 3 | 4 |
|---|---|---|---|---|
| No./3 | 0.9 | 1.5 | 2.4 | 3 |
| No./1 | 0.3 | 0.5 | 0.8 | 1 |
| R | 0.21 | 0.21 | 0.185 | 0.18 |
| N (No./1.75) | 0.525 | 0.875 | 1.4 | 1.75 |
| RN | 0.11 | 0.18 | 0.259 | 0.315 |
| E | 0.086 | 0.052 | 0.036 | 0.03 |

Testing the springback for the four prostheses, the following values were determined:

| Test | $\theta_B$ | 1 Angle | 2 Angle | 3 Angle | 4 Angle | Straight Angle |
|---|---|---|---|---|---|---|
| 1 | 30 | 5° | 3° | 3° | 2° | 6° |
|   | 60 | 12° | 15° | 11° | 11° | 22° |
|   | 90 | 22° | 25° | 22° | 23° | 39° |
|   | 120 | 40° | 41° | 38° | 33° | 51° |
| 2 | 30 | 4° | 5° | 5° | 4° | 4° |
|   | 60 | 13° | 15° | 9° | 15° | 19° |
|   | 90 | 25° | 30° | 24° | 24° | 38° |
|   | 120 | 43° | 41° | 36° | 33° | 51° |
| 3 | 30 | 4° | 11° | 2° | 8° | 7° |
|   | 60 | 18° | 16° | 10° | 15° | 21° |
|   | 90 | 36° | 30° | 26° | 30° | 38° |
|   | 120 | 46° | 43° | 41° | 38° | 53° |

| $\theta_B$ | 1 Avg. | 2 Avg. | 3 Avg. | 4 Avg. | Straight Avg. |
|---|---|---|---|---|---|
| 30 | 4.3 | 6.3 | 3.3 | 4.7 | 5.7 |
| 60 | 14.3 | 15.3 | 10.0 | 13.7 | 20.7 |
| 90 | 27.7 | 28.3 | 24.0 | 25.7 | 38.3 |
| 120 | 43 | 41.7 | 38.3 | 34.7 | 51.7 |

| $\theta_B$ | 1 Avg. % | 2 Avg. % | 3 Avg. % | 4 Avg. % | Straight Avg. % |
|---|---|---|---|---|---|
| 30 | 14.3 | 21.1 | 11.0 | 15.6 | 18.9 |
| 60 | 23.8 | 25.6 | 16.7 | 22.8 | 34.4 |
| 90 | 30.8 | 31.5 | 26.7 | 28.5 | 42.6 |
| 120 | 35.8 | 34.7 | 32.0 | 28.9 | 43.0 |

The fatigue life for the prostheses was determined as follows:

| Fatigue Life-Cycles | 1 | 2 | 3 | 4 | Straight |
|---|---|---|---|---|---|
| 1st Strand Breaking | 544 | 500 | — | 722 | 476 |
| Full Break | 661 | 596 | 647 | 969 | 512 |

Figures 11, 12:
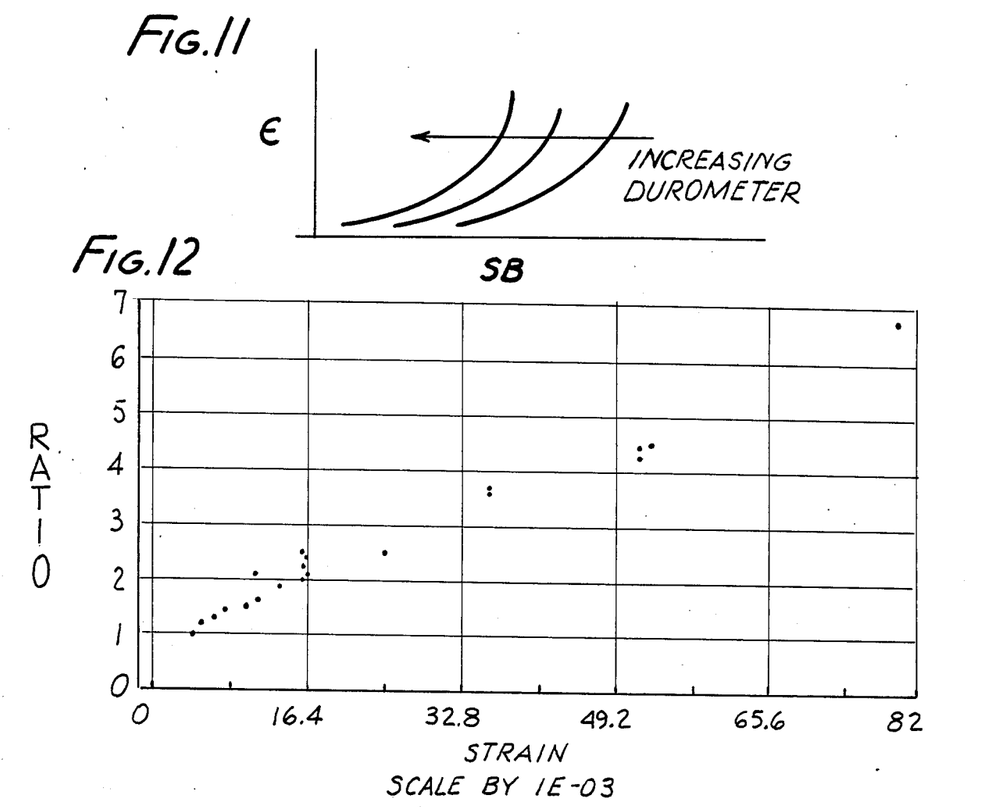
FIG. 11 is a graphical illustration of a family of curves showing the relationship between strain and spring back as a function of the durometer of the body of a prosthesis.
FIG. 12 is a graphical illustration showing the relationship between the ratio of the actual strain to the predicted strain as plotted against the actual strain.

Additional prototypes of implantable prostheses having a metal coil imbedded within the prostheses were constructed using silicone-bodied prosthesis having lower and lower durometers. As a result of the tests, a family of asymtotic curves were developed based upon the durometer of the body of the prosthesis when the strain was plotted against springback. A family of curves is illustrated in FIG. 11.

The following table is a tabulation of data collected imperically and predicted using the above derived equations for a number of implantable penile prosthesis prototypes.

| P | B | Ftgue | Strain | P-Str | Ratio | Defltn | PPH | S | MxSB % | L | N/In |
|---|---|---|---|---|---|---|---|---|---|---|---|
| 1 | A | 6891 | .0062 | .005 | 1.24 | .0299 | 10 | 9 | 3.33 | L | 2.9 |
| 2 | B | 387 | .052 | .0125 | 4.16 | .0075 | 10 | 9 | 38.3 | L | 0 |
| 3 | C | 2640 | .0107 | .0065 | 1.65 | .0123 | 9.8 | 9 | 20 | L | 2.83 |
| 4 | C | 1685 | .014 | .0075 | 1.87 | .0173 | 9.8 | 9 | 17.78 | L | 1.9 |
| 5 | C | — | .0161 | — | — | .0174 | 9.8 | 9 | 25.56 | L | 1.47 |
| 6 | D | 544 | .0807 | .012 | 6.73 | .0065 | 9 | 9 | 35.83 | L | .33 |
| 7 | D | 500 | .0533 | .012 | 4.44 | .0089 | 9 | 9 | 34.72 | L | .5 |
| 8 | D | 647 | .0358 | .01 | 3.58 | .0281 | 9 | 9 | 31.94 | L | .743 |
| 9 | D | 722 | .0249 | .01 | 2.49 | .0091 | 9 | 9 | 28.89 | L | 1.07 |
| 10 | D | 476 | .052 | .012 | 4.33 | .0064 | 9 | 9 | 43.06 | L | 0 |
| 11 | E | 3238 | .0533 | .0062 | 8.60 | .0226 | 5 | 9 | 48.33 | L | .5 |
| 12 | E | 0 | .0533 | 78 | 0.00 | .0248 | 5 | 9 | 47.22 | L | .5 |
| 13 | E | 860 | .0358 | .0097 | 3.69 | .0262 | 5 | 9 | 46.66 | L | .743 |
| 14 | E | 3450 | .052 | .0062 | 8.39 | .0179 | 5 | 9 | 54.72 | L | 0 |
| 15 | F | 1465 | .0166 | .008 | 2.08 | — | 5 | 9 | 48.33 | L | 1.6 |
| 16 | F | 3108 | .0108 | .0064 | 1.69 | — | 5 | 9 | 43.89 | L | 2.46 |
| 17 | F | 0 | .005 | 9 | 0.00 | — | 5 | 9 | 17.22 | L | 5.3 |
| 18 | G | 5457 | .0533 | .0052 | 10.25 | .0197 | 5 | 9 | 49.72 | L | .5 |
| 19 | G | 1395 | .0166 | .008 | 2.08 | .0197 | 5 | 0 | 44.17 | L | 1.6 |
| 20 | G | 6894 | .0108 | .005 | 2.16 | .0187 | 5 | 9 | 46.94 | L | 2.46 |
| 21 | H | 2305 | .0166 | .007 | 2.37 | .0125 | 5 | 9 | 51.39 | R | 1.6 |
| 22 | H | 1131 | .0166 | .0087 | 1.91 | .0149 | 5 | 9 | 45 | L | 1.6 |
| 23 | H | 1597 | .0166 | .0078 | 2.13 | .0177 | 5 | 9 | 40 | L | 1.6 |
| 24 | H | 1875 | .0166 | .0073 | 2.27 | .0188 | 5 | 9 | 44.72 | R | 1.6 |
| 1 | I | 1332 | .0168 | .0082 | 2.05 | .0302 | 5 | 9 | 68.61 | L | 1.6 |
| 2 | I | 1894 | .0167 | .0073 | 2.29 | .0166 | 5 | 9 | 63.33 | L | 1.6 |
| 3 | I | 3096 | .0161 | .0064 | 2.52 | .017 | 5 | 9 | 61.11 | L | 1.6 |
| 4 | J | 3114 | .0098 | .0064 | 1.53 | .0251 | 5 | 9 | 60.83 | L | 2.67 |
| 5 | J | 7081 | .0074 | .005 | 1.48 | .029 | 5 | 9 | 50.55 | L | 3.33 |
| 6 | J | 6324 | .0067 | .0052 | 1.29 | .0337 | 5 | 9 | 49.17 | L | 4 |
| 1 | K | 21700 | .00426 | .0042 | 1.01 | .0172 | 5 | 9 | 28.33 | R | 6.6 |
| 2 | K | 34134 | .00439 | .00415 | 1.11 | .0278 | 5 | 9 | 29.72 | R | 6 |
| 3 | K | 19028 | .00528 | .0046 | 1.15 | .0342 | 5 | 9 | 39.72 | R | 5.3 |

For the above-identified tabulation of data, the legend P=Penile; B=Batch; Ftgue=Fatigue; P-Strn=Predicted Strain; Defltn=Inches Per Gram Average Deflection; PPH=Parts Per Hundred Cross-Linker; MxSB%=Maximum Springback; L=Lay; and N/In=Number of Turns Per Inch.

In evaluating the data in the above table, various graphs were plotted. The ratio of the actual strain to the predicted strain was plotted versus the actual strain. The graph depicted in FIG. 12 shows such a plot. As can be seen from the graph, it appears as though a straight line function or that the predicted strain various from the strain by a constant error which can be formulated. Using regression analysis, the ratio was found to be $$\text{Ratio} = 71.038\epsilon + 0.874$$

and since $$\text{Ratio} = \epsilon/\epsilon_{Predicted}$$

substituting we have $$\epsilon/\epsilon_p = 71.038\epsilon + 0.874$$

or $\epsilon_P = \epsilon/(71.038\epsilon + 0.874)$ then we can use this value to work out a more accurate strain equation for:

$$\sigma_B = \frac{2\Delta Xr}{N\pi}\left(\frac{E}{2R^2} + \frac{G}{3R^2 + r^2}\right)$$

$$\Delta X = (\pi - \theta)R$$

and $$\epsilon = \frac{\sigma}{E} = \frac{2(\pi - \theta)Rr}{N\pi}\left(\frac{1}{2R^2} + \frac{G/E}{3R^2 + r^2}\right)$$

as $$G = \frac{E}{2(1 + \nu)}$$

then $$\epsilon = \frac{(\pi - \theta)Rr}{N\pi}\left(\frac{1}{R^2} + \frac{1}{(1 + \nu)(3R^2 + r^2)}\right)$$

Now, therefore, $$\sigma_{MAX} = 1.21\sigma_B$$

and, therefore, $$\epsilon_{MAX} = 1.21\epsilon_B$$

Thus, we have $\epsilon$ including the empirically derived constant to be $$\epsilon_P = \frac{1}{71.038 + \frac{0.874}{\epsilon}}$$

thus $$\epsilon_P = \frac{1}{71.038 + \frac{0.874}{\frac{(\pi - \theta)Rr}{N\pi}\left(\frac{1}{R^2} + \frac{1}{(1 + \nu)(3R^2 + r^2)}\right)}}$$

Figure 13:
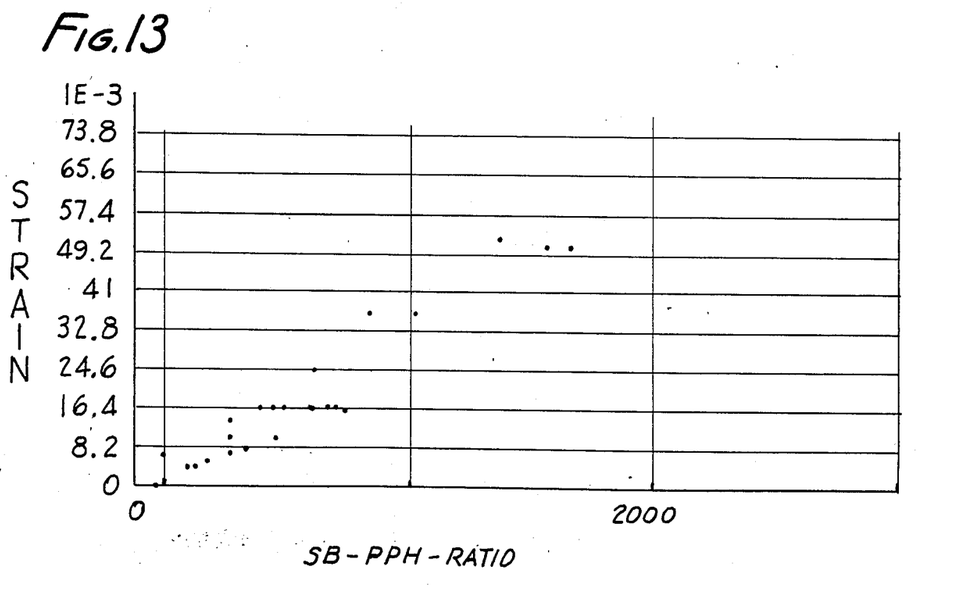
FIG. 13 is a graphical illustration of strain plotted versus spring back.

When the strain is plotted versus the springback, another linear relationship appears to be present as is shown in FIG. 13. From this figure, it appears that there is a relationship between the springback and the strain which is the predicted or calculated strain. Thus, the springback is also predictable or calculable. Using regression analysis, the springback. PPH.ratio is given as $$SB.PPH.\text{Ratio} = 26856.85\epsilon + 79.746$$

and $$\text{Ratio} = 71.038\epsilon + 0.874$$

Therefore, the $$SB = \frac{\left(\frac{26856.85\epsilon + 79.746}{71.038\epsilon + 0.874}\right)}{PPH}$$

Figure 10:
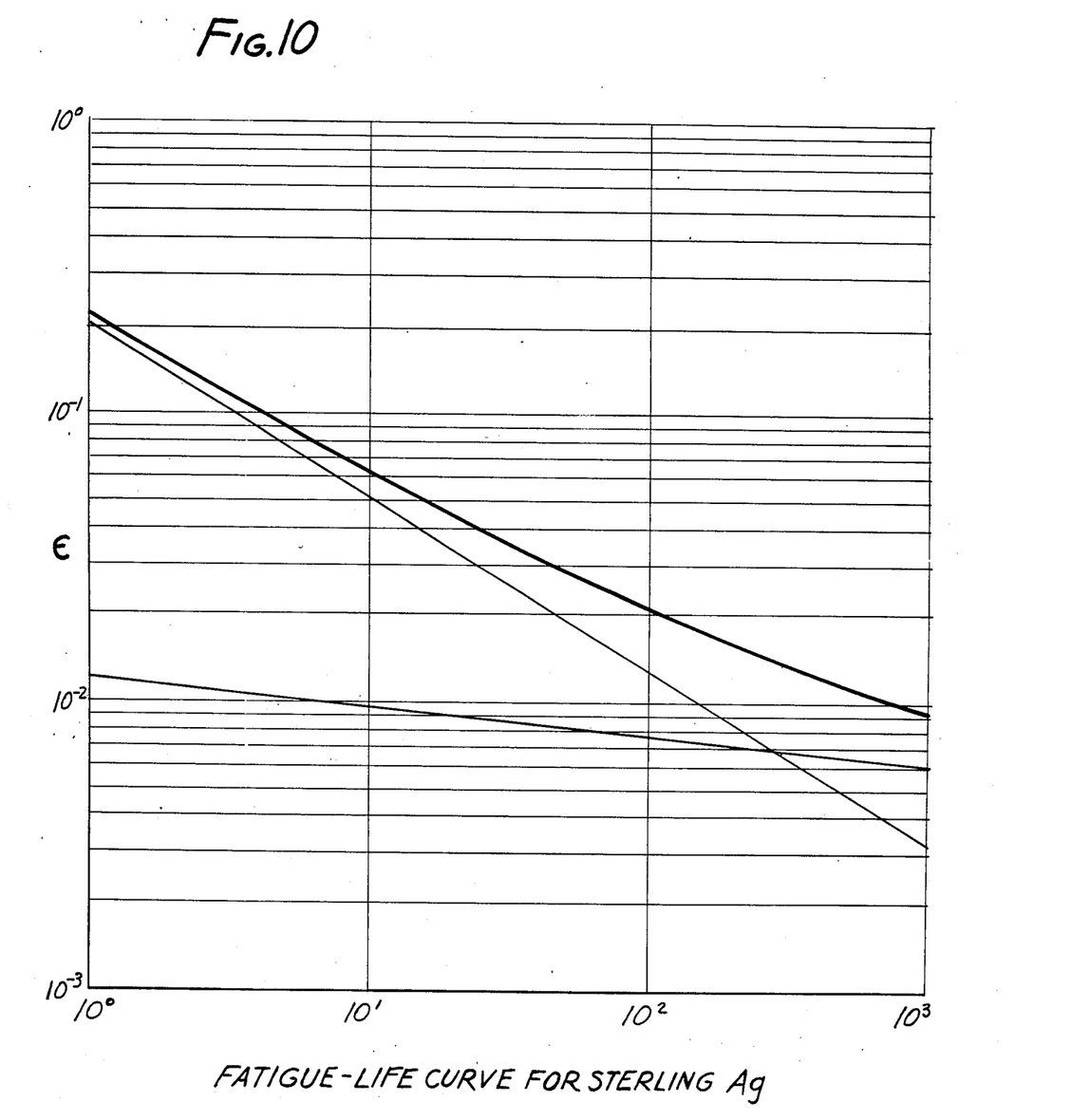
FIG. 10 is a graphical illustration of a fatigue life curve for sterling silver wire.
Figure 14:
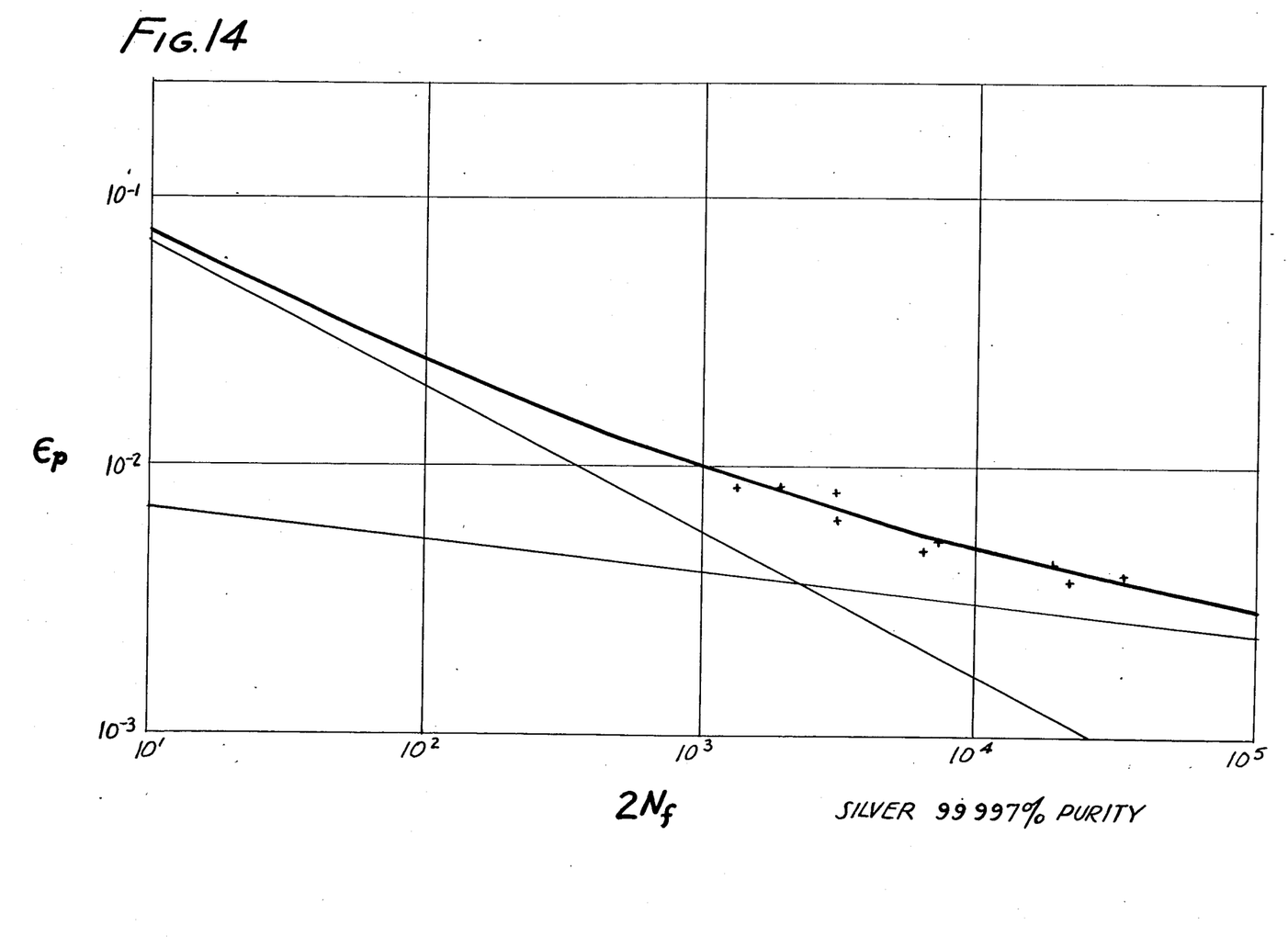
FIG. 14 is a graphical illustration of a fatigue life curve of 99.997% pure silver.

The earlier fatigue life curve shown in FIG. 10 is the fatigue life curve for sterling silver. Rather than use sterling silver as the coil in the prosthesis, it is desirable to use pure silver. To generate the fatigue life curve for pure silver, it was necessary to conduct tensile tests on silver. The results of the tensile tests are given as follows:

| Test | $\sigma$ | $\Delta L$ | $\epsilon$ | E | $\sigma_f$ | $\epsilon_f$ | $\Delta l_f$ | $P_f$ |
|---|---|---|---|---|---|---|---|---|
| 1 | 203718 | 0.398 | 0.066 | $3.07 \times 10^6$ | 25057 | 0.206 | 1.24 | 12.3 |
| 2 | 203718 | 0.4365 | 0.073 | $2.8 \times 10^6$ | 25057 | 0.223 | 1.34 | 12.3 |
| Avg. | | | | $2.9 \times 10^6$ | | 0.2145 | | | then $$\sigma_f/E = 0.0085$$

To determine the extrapolative fatigue, then $$\epsilon_t = \epsilon_f(2N_f)^c + \sigma_f/E(2N_f)^b$$

wherein $-0.5 \geq C \geq -0.7$ and $-0.08 \geq b \geq -0.12$

Using analysis on the nine determined empirical data points, it was found that for a minimum error $b = -0.11$ and $c = -0.524$ making the equation $$\epsilon_t = 0.2145(2N_f)^{-0.524} + 0.0085(2N_f)^{-0.11}$$

which is shown plotted in FIG. 14.

Fatigue life curves for other materials can be similarly plotted from the tensile strength test. After the fatigue life curves have been generated for the various materials, then penile prostheses using the various materials in coils can be constructed. For example, once a given fatigue life is selected by the person desiring to construct a penile prosthesis, the fatigue life curve is used to determine the strain for such a fatigue life. Then utilizing the above derived formula for the strain, a reverse calculation can be utilized to determine the proper R, r, and N in order to provide such a strain.

In selecting the characteristics and dimensions of an implantable positionable penile prosthesis having the characteristics described herein, one selects the desired life for the prosthesis; i.e., the desired number of bends which could bring about fatigue of the coil. Once the life is selected, then using a fatigue life curve for a given coil material, such as a nine strand silver braided wire, the allowable strain, $\epsilon$, can be determined. Using the equation $$\epsilon = \cfrac{1}{71.038 + \cfrac{0.874}{\cfrac{(\pi - \theta)Rr}{N\pi}\left(\cfrac{1}{R^2} + \cfrac{1}{(1 + \nu)(3R^2 + r^2)}\right)}}$$

From this equation, the relationship of N, R and r can be determined. It should also be recognized that $R_{MAX}$ is determined by the outer diameter of the penile prosthesis and that r is determined by the diameter of the cable comprising the coil. It is then recognized that springback is to be maximized in order to provide greatest positionability. By holding the above relationship constant and using the derived springback formula such as the formula derived for silver strand coil $$SB = \frac{\left(\frac{26856.85\epsilon + 79.746}{71.038\epsilon + 0.874}\right)}{PPH}$$

The parameters of the coil can be fully determined. That is, the N, R, and r dimensions can be selected.

However, it is to be noted that there are physical limitations with regard to the selection of R. That is, the radius of the coil within the prosthesis can only approach the radius of the prosthesis itself. Therefore, R is limited by the size of the prosthesis, which in turn is limited by the natural dimensions of the corpora cavernosum. Generally, implantable penile prostheses are constructed having a diameter of about 0.9 to about 1.3 centimeters. The radius of any coil implanted within the prosthesis then must be less than these values.

It is to be remembered above that the strain is indirectly related to the number of coils per length, directly related to the radius of the wire or braided wire comprising the coils, and inversely related to the square of the coil radius. In view of these relationships, it can be seen that it is desirable to select the radius of the wire or braided wire to be as small as possible and to select the number of coils to be as large as possible without sacrificing the desired springback. Using a prosthesis of a diameter of 0.9 to 1.3 centimeters (0.354–0.512 inches), it is preferable to select a radius for the coil such that the radius is from about 0.082 inches to about 0.165 inches. Using this preferred range for the radius, there can be sufficient encapsulation of the coil by the body of the prosthesis to provide a soft feeling prosthesis.

In an especially preferred embodiment of a positionable penile prosthesis herein which was constructed having a 1.1 centimeter diameter and a multi-stranded silver coil containing nine strands therein, the other variables were selected as follows:

N=0.9–1.5 coils to the inch or up to about 7 coils-/inch;
R=0.13585 inches; and
r=0.0125 inches.

Another embodiment of the penile prosthesis is shown in FIG. 2 wherein the coil is a multi-strand, braided-wire coil 24 within the prosthesis 20 and is surrounded by a mesh, such as a DACRON (trademark of DuPont) mesh 26. The mesh can be constructed of any suitable material compatible with the elastomeric body. It is preferred to have the metal coil encapsulated with a mesh as the mesh aids in the prevention of rupture of the outer body of the prosthesis when the coil itself fatigues and ruptures. The mesh can extend around the entire coil including the ends as the ends of the mesh can be overlapped and fastened such as by suturing to completely encapsulate the metal coil.

The prosthesis 20 also includes an elastic body portion 22 which is constructed of a suitable silicone elastomer. The prosthesis is molded in a manner such that the metal coil 24 and mesh 26 are completely encapsulated by the silicone with the silicone also extending around and through the center of the metal coil.

The metal coil is positioned in the prosthesis such that it is closer to the proximal end 27 of the prosthesis. The proximal end of the prosthesis has a generally rounded tip where as the distal end 28 of the prosthesis has a tapered sphero-conical shape.

FIG. 3 shows a cross section taken along lines 3—3 of FIG. 2. As can be seen in FIG. 3, the metal coil 24 is surrounded by the mesh 26. The elastic body 22 of the prosthesis surrounds the coil and fills the spaces within the coil.

Figure 15:
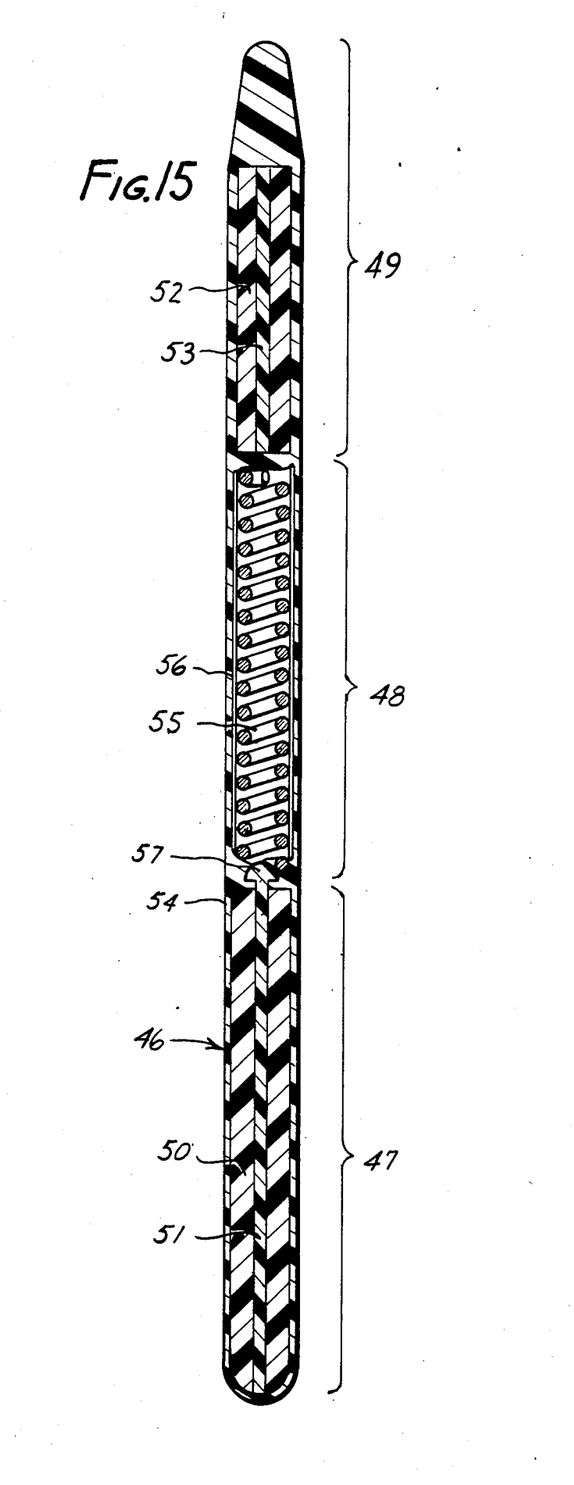
FIG. 15 is a cross-sectional view of an alternative embodiment of the prosthesis of the present invention.

FIG. 15 shows another embodiment of the improved penile prosthesis herein. The penile prosthesis 46 shown in FIG. 15 includes a proximal section 47, intermediate section 48, and distal section 49. Although the prosthesis can be provided in various lengths with each of the sections being of selected lengths. For an average length of 23 centimeters for a prosthesis, the proximal section is about 10 centimeters in length, the intermediate section about 6 centimeters, and the distal section about 7 centimeters in length. Such a prosthesis can be provided with a trimmable proximal section which can be trimmed to accomodate shorter lengths when needed.

The proximal section 47 includes a first inner elastomeric body portion 50. The first inner elastomeric body portion is constructed of an elastomeric material such as silicone and has a relatively high durometer to provide a stiffness to the proximal section. Preferably, the durometer of the first inner elastomeric body portion is about 65 Shore A. Extending through the first inner elastomeric body portion is an axially extending portion 51 of a relatively lower durometer elastomeric material. The axially extending portion 51 extends generally through the axial center of the first inner elastomeric body portion. In the preferred embodiment, the axially extending portion has a durometer of about 10 Shore A. The combination of the inner elastomeric body portion and axially extending portion combine to provide sufficient flexibility to the proximal section to approximate a naturally erected penis.

The distal section 49 also includes a second inner elastomeric body portion 52 having a relatively high durometer. The second inner elastomeric body portion also includes an axially extending portion 53 of low durometer elastomeric material extending through the axial center of the second inner elastomeric body portion. In the preferred embodiments, the second inner elastomeric body portion can be a silicone of a durometer of about 50 Shore A and the axially extending portion within the second inner elastomeric body portion can be a silicone having a durometer of about 10 Shore A.

The intermediate section 48 includes the metal coil or spring which can be a single strand or multi-strand braided wire spring 55. Preferably, a braided wire spring is used. Extending around the wire spring 55 is a mesh 56 such as a DACRON sheath which completely encapsulates the wire spring. The spring and mesh are also encapsulated in an elastomeric material such as silicone.

The first and second inner elastomeric body portions can be provided each with a head portion 57 as shown in FIG. 15 on only the first inner elastomeric portion. The head portion can provide a means for attachment of the inner elastomeric portion to the spring.

The entire prosthesis 46 is provided with an outer elastomeric body portion 54. The outer body portion can be a silicone elastomer of a relatively low durometer such as about 10 Shore A. The silicone extending around and encapsulating the braided wire spring can also be such a low durometer silicone elastomer as the outer elastomer body portion 54. Providing an outer elastomeric body portion of a relatively low durometer provides a feel and softness to the prosthesis to help in making the prosthesis approximate the natural penis and to promote tissue acceptance of the prosthesis when implanted.

As indicated above, the improved prostheses herein are implanted in the penis in pairs as is shown in FIG. 4. With reference to FIG. 4, two positionable prostheses 32 and 34 are positioned within the corpora cavernosa 36 and 38 of the penis 30. The proximal ends of each of the prostheses are positioned within each of the crus 42 and 44. The pubic symphysis 40 is shown also in FIG. 4.

Once the improved positionable penile prostheses herein are implanted, the normally flacid penis will present the appearance of an erect penis. The implanted positionable prostheses provide the ability to position the penis so as to conceal such an erect condition.

The improved positionable penile prosthesis herein provides an improvement over a nonpositionable penile prosthesis and over other known state of the art positionable prostheses as the prosthesis herein has a greater fatigue life so as to avoid breaking of the metal spring and subsequent erosion through the elastomeric body of the prosthesis.

I claim:

1. An implantable, positionable penile prosthesis having distal, intermediate and proximal sections comprising:
    a rod formed from an elastomeric material of a selected durometer;
    a metal multi-strand wire coil positioned within the intermediate section having a helical configuration with a plurality of coil sections extending about and defining an inner core area and coaxially embedded within at least a portion of the rod, the wire coil being embedded such that the elastomeric material extends between each coil section and through the inner core area of the wire coil and the coil having a coil radius, number of turns per unit length, and wire diameter which combines with the elastomeric material for substantially retaining the position into which the prosthesis is bent and for inhibiting fatigue of the metal wire coil when the prosthesis is repeatedly bent for positioning; and
    wherein the proximal section comprises an inner elastomeric body portion within an outer elastomeric body portion of different durometer.

2. An implantable, positionable penile prosthesis as recited in claim 1 wherein the elastomeric material comprises a silicone polymer.

3. An implantable, positionable penile prosthesis as recited in claim 1 wherein the metal wire coil is a braided, multi-strand wire coil.

4. An implantable, positionable penile prosthesis as recited in claim 1 or 3 wherein the metal of the metal wire coil comprises silver.

5. An implantable, positionable penile prosthesis as recited in claim 1 wherein the metal wire coil has a radius from about 0.082 to about 0.165 inches.

6. An implantable, positionable penile prosthesis as recited in claim 1 wherein the diameter of the metal wire of the coil is about 0.0125 inches.

7. An implantable, positionable penile prosthesis as recited in claim 1 wherein the metal wire coil comprises up to about 7 coils per inch axial length.

8. An implantable, positionable penile prosthesis as recited in claim 1 further comprising a sheath extending around the metal wire coil.

9. An implantable, positionable penile prosthesis as recited in claim 8 wherein the sheath comprises a DACRON mesh.

10. An implantable, positionable penile prosthesis as recited in claim 1 wherein the inner elastomeric body portion comprises a durometer of about 65 Shore A and the outer elastomeric body portion comprises a durometer of about 10 Shore A.

11. An implantable, positionable penile prosthesis as recited in claim 1 further comprising an axially extending elastomeric core portion positioned within and having a different durometer than the inner elastomeric body portion.

12. An implantable, positionable penile prosthesis as recited in claim 11 wherein the axially extending elastomeric core portion and outer elastomeric body portion comprise a durometer of about 10 Shore A and the inner elastomeric body portion comprises a durometer of about 65 Shore A.

13. An implantable, positionable penile prosthesis having a distal, intermediate and proximal sections comprising:
    a rod formed from an elastomeric material of a selected durometer; and
    a metal multi-strand wire coil positioned within the intermediate section having a helical configuration with a plurality of coil sections extending about and defining an inner core area and coaxially embedded within at least a portion of the rod, the wire coil being embedded such that the elastomeric material extends between each coil section and through the inner core area of the wire coil and the coil having a coil radius, number of turns per unit length, and wire diameter which combines with the elastomeric material for substantially retaining the position into which the prosthesis is bent and for inhibiting fatigue of the metal wire coil when the prosthesis is repeatedly bent for positioning; and
    wherein the distal section comprises an inner elastomeric body portion within an outer elastomeric body portion of different durometer.

14. An implantable, positionable penile prosthesis as recited in claim 13 wherein the inner elastomeric body portion comprises a durometer of about 65 Shore A and the outer elastomeric body portion comprises a durometer of about 10 Shore A.

15. An implantable, positionable penile prosthesis as recited in claim 13 further comprising an axially extending elastomeric core portion positioned within and having a different durometer than the inner elastomeric body portion.

16. An implantable, positionable penile prosthesis as recited in claim 15 wherein the axially extending elastomeric core portion and outer elastomeric body portion comprise a durometer of about 10 Shore A and the inner elastomeric body portion comprises a durometer of about 65 Shore A.

17. An implantable, positionable penile prosthesis as recited in claim 13 wherein the proximal section comprises an inner elastomeric body portion within an outer elastomeric body portion of different durometer.

18. An implantable, positionable penile prosthesis as recited in claim 17 wherein the inner elastomeric body portion comprises a durometer of about 65 Shore A and the outer elastomeric body portion comprises a durometer of about 10 Shore A.

19. An implantable, positionable penile prosthesis as recited in claim 17 further comprising an axially extending elastomeric core portion positioned within and having a different durometer than the inner elastomeric body portion.

20. An implantable, positionable penile prosthesis as recited in claim 19 wherein the axially extending elastomeric core portion and outer elastomeric body portion comprise a durometer of about 10 Shore A and the inner elastomeric body portion comprises a durometer of about 65 Shore A.

21. An implantable, positionable penile prosthesis as recited in claim 13 further comprising an inner elastomeric body portion within each of the distal and proximal sections, which inner elastomeric body portion lies within an outer elastomeric body portion of different durometers.

22. An implantable, positionable penile prosthesis as recited in claim 21 further comprising an axially extending elastomeric core portion within each of the inner elastomeric body portions of the distal and proximal sections, which axially extending elastomeric core portion has a different durometer than the inner elastomeric body portions.

23. An implantable, positionable penile prosthesis as recited in claim 13 further comprising a sheath extending around the metal wire coil.

24. An implantable, positionable penile prosthesis as recited in claim 23 wherein the sheath comprises a DACRON mesh.

25. An implantable, positionable penile prosthesis having distal, intermediate and proximal sections comprising:
 a rod formed from an elastomeric material of a selected durometer and having an inner elastomeric body portion within each of the distal and proximal sections, which inner elastomeric body portion lies within an outer elastomeric body portion of different durometer;
 a metal multi-strand wire coil positioned within the intermediate section having a helical configuration with a plurality of coil sections extending about and defining an inner core area and coaxially embedded within at least a portion of the rod, the wire coil being embedded such that the elastomeric material extends between each coil section and through the inner core area of the wire coil and the coil having a coil radius, number of turns per unit length, and wire diameter which combines with the elastomeric material for substantially retaining the position into which the prosthesis is bent and for inhibiting fatigue of the metal wire coil when the prosthesis is repeatedly bent for positioning; and
 wherein the proximal section comprises an inner elastomeric body portion within an outer elastomeric body portion of different durometer.

26. An implantable, positionable penile prosthesis as recited in claim 25 wherein the elastomeric material comprises a silicone polymer.

27. An implantable, positionable penile prosthesis as recited in claim 25 wherein the metal wire coil is a braided, multi-strand wire coil.

28. An implantable, positionable penile prosthesis as recited in claim 25 or 27 wherein the metal of the metal wire coil comprises silver.

29. An implantable, positioned penile prosthesis as recited in claim 25 wherein the metal wire coil has a radius from about 0.082 to about 0.165 inches.

30. An implantable, positionable penile prosthesis as recited in claim 25 wherein the diameter of the metal wire of the coil is about 0.0125 inches.

31. An implantable, positionable penile prosthesis as recited in claim 25 wherein the metal wire coil comprises up to about 7 coils per inch axial length.

32. An implantable, positionable penile prosthesis as recited in claim 25 further comprising a sheath extending around the metal wire coil.

33. An implantable, positionable penile prosthesis as recited in claim 32 wherein the sheath comprises a DACRON mesh.

34. An implantable, positionable penile prosthesis as recited in claim 25 wherein the inner elastomeric body portion comprises a durometer of about 65 Shore A and the outer elastomeric body portion comprises a durometer of about 10 Shore A.

35. An implantable, positionable penile prosthesis as recited in claim 25 further comprising an axially extending elastomeric core portion within each of the inner elastomeric body portions of the distal and proximal sections, which axially extending elastomeric core portion has a different durometer than the inner elastomeric body portions.

* * * * *